US008447012B2

(12) United States Patent
Ichizawa et al.

(10) Patent No.: US 8,447,012 B2
(45) Date of Patent: May 21, 2013

(54) RADIATION INSPECTION APPARATUS

(75) Inventors: Yasushi Ichizawa, Musashino (JP); Hirohiko Obinata, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 387 days.

(21) Appl. No.: 12/834,537

(22) Filed: Jul. 12, 2010

(65) Prior Publication Data

US 2011/0013748 A1    Jan. 20, 2011

(30) Foreign Application Priority Data

Jul. 16, 2009  (JP) ................................. 2009-167875

(51) Int. Cl.
*H05G 1/52* (2006.01)

(52) U.S. Cl.
USPC ......................................................... 378/113

(58) Field of Classification Search
USPC .................. 378/108, 113, 114, 138
See application file for complete search history.

(56) References Cited

U.S. PATENT DOCUMENTS

| 4,180,737 A * | 12/1979 | Kingsley | 250/367 |
|---|---|---|---|
| 4,727,561 A * | 2/1988 | Fujisaki | 378/54 |
| 4,933,960 A * | 6/1990 | Fujisaki | 378/53 |
| 5,097,494 A * | 3/1992 | Pantelleria et al. | 378/110 |
| 6,404,851 B1 * | 6/2002 | Possin et al. | 378/98.7 |
| 2001/0038681 A1 * | 11/2001 | Stanton et al. | 378/55 |

FOREIGN PATENT DOCUMENTS

| JP | 5683333 A | 7/1981 |
|---|---|---|
| JP | 59207134 A | 11/1984 |
| JP | 6272328 A | 4/1987 |
| JP | 63181740 A | 7/1988 |
| JP | 1161712 UM | 11/1989 |
| JP | 11-128217 A | 5/1999 |
| JP | 2000135268 A | 5/2000 |
| JP | 2001-198119 A | 7/2001 |
| JP | 2002320607 A | 11/2002 |
| JP | 2004108871 A | 4/2004 |
| JP | 2009085876 A | 4/2009 |

OTHER PUBLICATIONS

Japanese Office Action corresponding to Japanese Patent Application No. 2009-167875, mailed May 6, 2011.

* cited by examiner

*Primary Examiner* — Irakli Kiknadze
(74) *Attorney, Agent, or Firm* — Sughrue Mion, PLLC

(57) ABSTRACT

A radiation inspection apparatus includes a radiation source, a measurement radiation detecting unit being a rectangle having a long side, and a reference radiation detecting unit that is disposed between the radiation source and an inspection target, the reference radiation detecting unit being disposed near a path of a radiation from the radiation source to the measurement radiation detecting unit not to interrupt the radiation from the radiation source to the measurement radiation detecting unit. An intensity of the radiation source are corrected by calculating a change value of the intensity and the intensity distribution from an output of the reference radiation detecting unit and by correcting the output of the measurement radiation detecting unit based on the change value.

17 Claims, 7 Drawing Sheets

RADIATION INSPECTION APPARATUS

BACKGROUND OF THE INVENTION

1. Field of the Invention

The present invention generally relates to a radiation inspection apparatus that uses an ionizing radiation such as an X-ray, a beta radiation, and a gamma radiation. More specifically, the present invention relates to a radiation inspection apparatus including a reference detecting element, which corrects an intensity distribution and an intensity variation of an ionizing radiation, which has been radiated from a radiation source, based on an intensity of the ionizing radiation detected by the reference detecting element.

Priority is claimed on Japanese Patent Application No. 2009-167875, filed Jul. 16, 2009, the content of which is incorporated herein by reference.

2. Description of the Related Art

In recent years, there has been performed a radiation inspection, which detects an X-ray or a soft X-ray, for example, in various fields of research or inspection of foods, industrials, medical techniques, securities, and so on. In the fields of inspection, it is determined whether or not there is a certain object or a defect in an inspection target by watching a gray image that is relatively sharp. In a specific field of industrials, medical techniques, and so on, the determination may be performed based on the gray image, which gray is relatively light, by a doctor or a laboratory technician. The doctor or the laboratory technician watches the gray image using a display monitor, and performs the determination comprehensively and selectively, considering various elements such as an uneven brightness of the display monitor, an uneven brightness of an image pick-up system, and a trend or a visible characteristic that is peculiar to the inspection target.

On the other hand, if the determination is performed by an auto inspection, not by a human's visual inspection, then various corrections are necessary such as a correction of the uneven brightness of the image pick-up system, a correction of a detection sensitivity, a correction of the trend that is peculiar to the inspection target, an emphasis of a gray value of the gray image, and an image processing that effectively extracts a characteristic of parts of the inspection target.

In the descriptions below, an ionizing radiation will hereinafter be referred to as an X-ray for an example. In the inspection using the X-ray, the gray image is acquired by setting the inspection target such as a product and a body between an X-ray source and a detecting apparatus and by detecting the intensity of the X-ray based on a transmissivity of the X-ray, in general. Therefore, the stability of the X-ray source is very important. If the intensity of the X-ray source is changed or losing stability, then the instability of the intensity of the X-ray source influences a detected image or the accuracy of the detection directly.

To make the X-ray source drive in stable, a feedback control, a temperature control, and a monitoring of an X-ray value are performed. Depression of the X-ray value of the X-ray that the X-ray source irradiates cannot be neglected, for an X-ray tube used in the X-ray source is short-lived. For example, Japanese Unexamined Patent Application, First Publications, No. 2001-198119 discloses a method of monitoring the X-ray value and feed back the monitoring result to a measurement system.

FIG. 6A is a view illustrating a configuration structure of a reference detecting element in an X-ray inspection apparatus disclosed in Japanese Unexamined Patent Application, First Publications, No. 2001-198119. The X-ray inspection apparatus includes an X-ray source 3, a rotary part 2, an X-ray detector 11, and a reference detecting element 12. The rotary part 2 includes an opening 2h where an inspection target 9 is set. The reference detecting element 12 detects the intensity of the X-ray irradiated from the X-ray source 3 so as to correct the intensity variation of the X-ray irradiated from the X-ray source 3. The reference detecting element 12 is disposed on a line segment L that connects a focus of the X-ray source 3 and the outer periphery of the opening 2h of the rotary part 2 or outside of the line segment L, and is disposed on an extension circular arc of an alignment circular arc of the detecting element in the X-ray detector 11.

The length of the X-ray detector 11 is adjusted so that both ends of the X-ray detector 11 are disposed on the line segment L that connects the focus of the X-ray source 3 and the outer periphery of the opening 2h of the rotary part 2 or outside of the line segment L. The reference detecting element 12 is disposed on the both ends of the X-ray detector 11.

The X-ray is irradiated from the X-ray source 3 and detected by the X-ray detector 11 and the reference detecting element 12. The X-ray that enters the reference detecting element 12 passes through the outside of the opening 2h. The inspection target 9 is not disposed on a path of the X-ray from the focus of the X-ray source 3 to the reference detecting element 12. Therefore, the inspection target 9 does not interfere with the detection by the reference detecting element 12. The distance between the focus of the X-ray source 3 and the reference detecting element 12 is equal to the distance between the focus of the X-ray source 3 and the X-ray detector 11. Therefore, the quality of the X-ray that enters the reference detecting element 12 is equal to the quality of the X-ray that enters the X-ray detector 11.

FIG. 6B is a block diagram illustrating a configuration structure of the reference detecting element in the X-ray inspection apparatus disclosed in Japanese Unexamined Patent Application, First Publications, No. H11-128217. The X-ray inspection apparatus includes an X-ray tube 1, an X-ray detection unit 20, a calculation unit 23, a memory 24, a display unit 25, and an X-ray control unit 26. The inspection target 9 is disposed between the X-ray tube 1 and the X-ray detection unit 20. The X-ray is irradiated from the X-ray tube 1 to the inspection target 9. The X-ray tube 1 and the X-ray detection unit 20 are integrated to be rotated, so that X-ray scanning data of the inspection target 9 can be acquired in the direction of 360 degrees or 180 degrees.

The X-ray detection unit 20 includes a collimator 21 and an X-ray detector 22. The collimator 21 collimates an incident X-ray. The X-ray detector 22 detects the X-ray. The collimator 21 and the X-ray detector 22 are in a shape of circular arc having its center at the X-ray tube 1. The X-ray detector 22 includes channels of X-ray detecting elements which are disposed in a shape of circular arc having its center at the X-ray tube 1. The number of the channels of the X-ray detecting elements is from 500 to 1000. The X-ray detecting element includes a scintillator element, which converts the X-ray to a light, and a photodiode that detects the light, which has been converted by the scintillator element, to output an electrical signal. The scintillator element and the photodiode are not illustrated in the figures. The X-ray detector 22 includes imaging X-ray detecting channels 22a, reference channels 22b, and monitoring X-ray detecting channels 22c. The reference channels 22b and the monitoring X-ray detecting channels 22c are disposed at both ends of the X-ray detector 22.

The reference channel 22b is for measuring the intensity of the X-ray from the X-ray tube 1 that has not transmitted through the inspection target 9. The monitoring X-ray detecting channel 22c is for detecting the movement of the focus of the X-ray tube 1.

The calculation unit 23 calculates data for generating X-ray image based on a detection value by the X-ray detection unit 20. The calculation unit 23 outputs a command signal to each unit of the X-ray inspection apparatus including the X-ray control unit 26. The display unit 25 displays the X-ray image such as a cross-sectional image.

In the above examples, the X-ray inspection apparatus is supposed to be the X-ray CT apparatus. Therefore, the distances between the X-ray source and the detecting unit are the same. FIG. 7 is a perspective view illustrating the configuration structure of the X-ray inspection apparatus when an inspection target 32 is sheet-shaped and is measured by a measurement X-ray line sensor 31 disposed in planate. In this case, the inspection target 32 is a paper or a sheet that is produced by a line production for an industrial use. The width of the inspection target 32 is a few meters, for example. The X-ray is irradiated from an X-ray source 30. The X-ray is transmitted through the inspection target 32 and detected by the measurement X-ray line sensor 31 disposed in planate.

In the industrial use, the inspection target 32 is transmitted through a previous process, an inspection process, and a post process by the line production in planate. Therefore, it is difficult to make only the inspection apparatus arranged in the shape of circular arc.

If the planate line sensor is used, then the distance between the X-ray source and the inspection target at a center portion are different from the distance between the X-ray source and the inspection target at a peripheral portion. Similarly, the distance between the detecting unit and the inspection target at a center portion are different from the distance between the detecting unit and the inspection target at a peripheral portion. The X-ray, especially the soft X-ray, is influenced by air absorption, temperature, humidity and atmosphere. The X-ray near the reference unit, which is distant from the detecting unit, is inclined to be different from the X-ray near the detecting unit. The incident angles of the detecting unit may be variable.

The X-ray is radically diffused from the X-ray source. The reference detecting unit, which is disposed near the peripheral portion, is away from the measurement detecting unit, which is disposed near the center portion. Therefore, it is not suitable to correct the X-ray value of the measurement detecting unit based on the X-ray value of the reference detecting unit. The correction is performed by estimating the change of the X-ray value of the measurement detecting unit from the change of the X-ray value of the reference detecting units, which are disposed at both ends of the measurement detecting unit, under the assumption that the distribution of the X-ray from the X-ray source does not change.

SUMMARY

In the present invention, a reference detecting unit is disposed near a detecting unit and between the detecting unit and an X-ray source. The reference detecting unit corrects all X-ray values detected by the detecting unit. If necessary, the change of the radial distribution of the X-ray form the X-ray source is corrected in real time. Then, the measurement can be achieved highly accurately.

A radiation inspection apparatus that inspects an inspection target using a radiation from a radiation source may include a measurement radiation detecting unit that detects the radiation, a reference radiation detecting unit that detects the radiation from the radiation source, the reference radiation detecting unit being disposed between the radiation source and the inspection target, a calculation unit that calculates a change value of the intensity of the radiation based on an output of the reference radiation detecting unit, and a radiation control unit that corrects the intensity of the radiation by correcting an output of the measurement radiation detecting unit based on the change value.

The radiation inspection apparatus may further include a radiation source unit that irradiates the radiation radially.

The measurement radiation detecting unit may be a line sensor.

The reference radiation detecting unit may be adjacent to a path of the radiation from the radiation source to the measurement radiation detecting unit to prevent the reference radiation detecting unit from interrupting the radiation from the radiation source to the measurement radiation detecting unit.

The measurement radiation detecting unit and the reference radiation detecting unit may share a same hardware component.

The reference radiation detecting unit may be in a rectangle shape and different from the measurement radiation detecting unit in a size, a pitch and a length of a detecting element.

The reference radiation detecting unit may be a photosensor including a scintillator.

A time-series variation of the output of the reference radiation detecting unit may be calculated in real time, and the output of the measurement radiation detecting unit may be corrected in real time based on a calculation result of the time-series variation of the output of the reference radiation detecting unit.

A time-series variation of the output of the reference radiation detecting unit may be calculated at a constant period, and the output of the measurement radiation detecting unit may be corrected based on a same correction value of a calculation result of the time-series variation of the output of the reference radiation detecting unit till a next calculation of the time-series variation of the output of the reference radiation detecting unit is performed.

A sealed structure may be disposed between the radiation source and the inspection target. The sealed structure may be filled with a gas. The sealed structure may include an entrance window of the radiation from the radiation source, a first exit window that outputs the radiation for measurement detecting to the measurement radiation detecting unit, and a second exit window that outputs the radiation for reference detecting to the reference radiation detecting unit.

A first distance between the first exit window and the measurement radiation detecting unit may be equal to a second distance between the second exit window and the reference radiation detecting unit.

A collimator may be disposed adjacent to the radiation source, and the collimator may include a first irradiating window that outputs the radiation for measurement detecting and a second irradiating window that outputs the radiation for reference detecting.

If the radiation source is made of a radiation tube in reflection type that irradiates the radiation and a radiation target that reflects the radiation from the radiation tube and a sheet-shaped object is used as the inspection target, then a reflection surface of the radiation target may be nearly parallel to a direction of a movement of the sheet-shaped object, the radiation being reflected by the reflection surface.

The reference radiation detecting unit may be moved in one of a direction that is parallel to at least one of a long side of the measurement radiation detecting unit and a row of a plurality of photodiodes and a direction that is nearly perpendicular to a movement of the inspection target. The output of the reference radiation detecting unit may be stored in a storage unit as measurement data every time the reference radiation detecting unit is moved. A measurement error of the reference radiation detecting unit may be calculated based on more than one of the measurement data of the reference radiation detecting unit. If time-series variation of the intensity distribution of the radiation source is confirmed, then the output of the measurement radiation detecting unit may be corrected based on the time-series variation, the intensity distribution being acquired by deducting the measurement error from the measurement data of the reference radiation detecting unit.

The reference radiation detecting unit may be moved by one of an intermittent feeding and a periodic continuous reciprocating feeding. The intensity distribution of the radiation source may be calculated based on more than one of the measurement data at different areas of the reference radiation detecting unit at nearly a same time.

The number of movement of the reference radiation detecting unit may be measured at a plurality of measurement points. The plurality of measurement points may be determined based on a mechanism of the reference radiation detecting unit. The reference radiation detecting unit may stop at each of the plurality of measurement points. The intensity distribution of the radiation source may be calculated based on more than one of the measurement data at the plurality of measurement points.

The reference radiation detecting unit may continuously move. The number of movement of the reference radiation detecting unit may be measured at different measurement points. The intensity distribution of the radiation source may be calculated based on more than one of the measurement data at the different measurement points.

More than one of the measurement data may be averaged by at least one of a least squares method, an average value, moving average deviations, and combinations of more than one of the least squares method, the average value and the moving average deviations, so as to calculate a center value with a minimum of deviation. The intensity distribution of the radiation source may be acquired based on a temporal variation of the center value.

A radiation inspection apparatus that inspects an inspection target using a radiation from a radiation source may include a measurement radiation detecting unit that detects the radiation, and a reference radiation detecting unit that detects the radiation from the radiation source, the reference radiation detecting unit being disposed between the radiation source and the inspection target, the reference radiation detecting unit being adjacent to a path of the radiation from the radiation source to the measurement radiation detecting unit to prevent the reference radiation detecting unit from interrupting the radiation from the radiation source to the measurement radiation detecting unit.

A radiation inspection apparatus that inspects an inspection target using a radiation from a radiation source may include a calculation unit that calculates a change value of the intensity of the radiation based on a radiation for reference detecting, and a radiation control unit that corrects the intensity of the radiation by correcting a radiation for measurement detecting based on the change value.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE PREFERRED EMBODIMENTS

The present invention will be now described herein with reference to illustrative embodiments. Those skilled in the art will recognize that many alternative embodiments can be accomplished using the teaching of the present invention and that the present invention is not limited to the embodiments illustrated for explanatory purpose.

In the descriptions below, an X-ray is used in a radiation inspection apparatus in accordance with the preferred embodiments of the present invention, but an ionizing radiation used in the radiation inspection apparatus in accordance with the preferred embodiments of the present invention is not limited to the X-ray, but may be any kinds of ionizing radiations such as beta radiation, gamma radiation, and so on.

First Preferred Embodiment

Figure 1A:
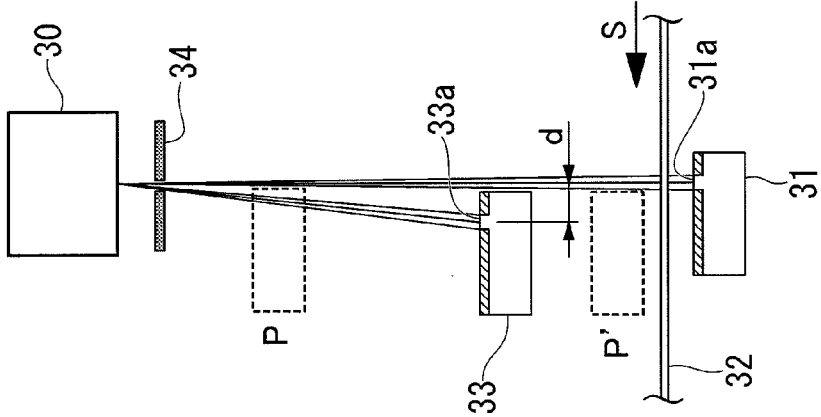
FIG. 1A is an elevation view illustrating an X-ray inspection apparatus in accordance with a first preferred embodiment of the present invention.
Figure 1B:
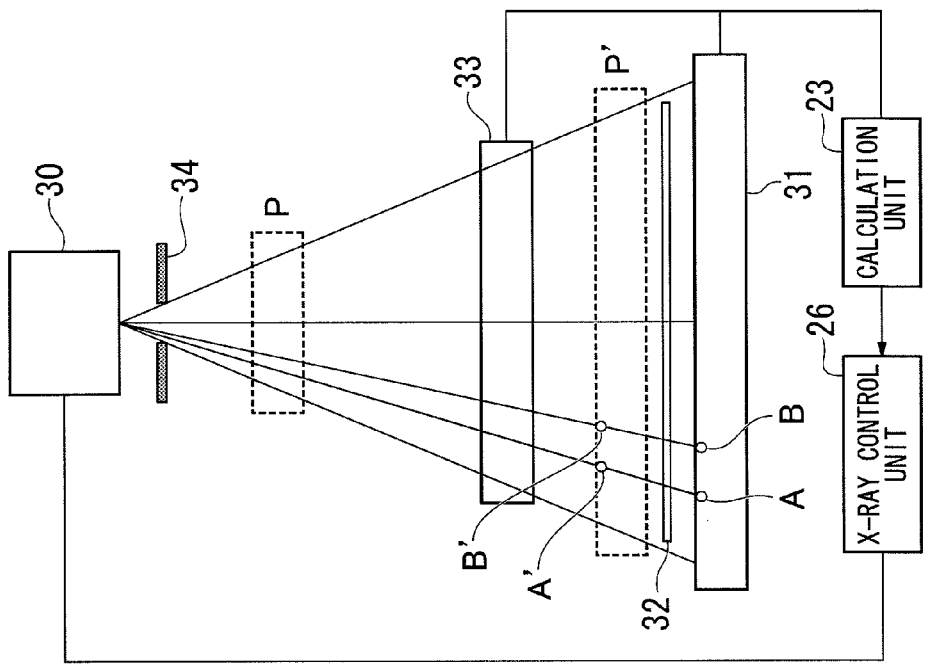
FIG. 1B is a side elevation view illustrating the X-ray inspection apparatus of FIG. 1A.

A first preferred embodiment of the present invention will be described. FIG. 1A is an elevation view illustrating an X-ray inspection apparatus in accordance with the first preferred embodiment of the present invention. FIG. 1B is a side elevation view illustrating the X-ray inspection apparatus of FIG. 1A. The X-ray inspection apparatus includes an X-ray source 30, a measurement X-ray line sensor 31 that is disposed facing with the X-ray source 30, a reference X-ray line sensor 33 that is different from the measurement X-ray line sensor 31, a collimator 34 that is disposed near the X-ray source 30, a calculation unit 23 and an X-ray control unit 26. The measurement X-ray line sensor 31 is hereinafter referred to as the measurement sensor 31. The reference X-ray line sensor 33 is hereinafter referred to as the reference sensor 33. An inspection target 32 is set near the measurement sensor 31 and distant from the X-ray source 30. The inspection target 32 is moved in a direction S that is nearly perpendicular to a path of the X-ray, and is inspected or measured by the measurement sensor 31. The collimator 34 may include, or may not include, one or two transmission units, a measurement X-ray irradiating window and a reference X-ray irradiating window. The measurement sensor 31 includes an entrance window 31a from which the X-ray enters. The reference sensor 33 includes an entrance window 33a from which the X-ray enters.

The difference between the first preferred embodiment of the present invention and the prior art is that the reference sensor 33 is disposed in the first preferred embodiment of the present invention. The reference sensor 33 is different from the measurement sensor 31. The reference sensor 33 detects the X-ray before transmitting through the inspection target 32, as illustrated in FIG. 1B. The reference sensor 33 is disposed between a position P that is near the X-ray source 30 and a position P' that is near the inspection target 32. A distance d between a center of the entrance window 31a and a center of the entrance window 33a is made as small as possible under the condition that the X-ray that enters the measurement sensor 31 is not interrupted by the reference sensor 33.

The measurement sensor 31 includes detecting elements that are arranged along with the entrance window 31a. The reference sensor 33 includes detecting elements that are arranged along with the entrance window 33a. The number of channels of the detecting elements is from 500 to 1000. The detecting elements may be the same as each other. The detecting elements may be a combination of a supersensitive photodiode and a scintillator or may include another scintillator sheet. The size of the detecting elements or the number of the detecting elements may be different from each other. The difference of the output power of the detecting elements is corrected and then stored in a storage medium such as a memory.

The width of the area that the reference sensor 33 detects needs to be equal to or more than the width of the area that the measurement sensor 31 detects. The reference sensor 33 is set between the position P and the position P', and the necessary width of the area that the reference sensor 33 detects varies by the position where the reference sensor 33 is set. The reference sensor 33 may be short and inexpensive, or may be highly accurate and have a high stability.

If the reference sensor 33 that is the same with the measurement sensor 31 is disposed at the position P' that is nearest from the inspection target 32, then the reference sensor 33 corresponds to the measurement sensor 31 nearly one to one, and the intensity distribution or the uniformity of the X-ray can be acquired so as to correct the measurement value of each measurement detecting element.

A pixel A and a pixel B is disposed on the measurement sensor 31. A pixel A' is at a cross point of the reference sensor 33 and a line that connects between the pixel A and the X-ray source 30. A pixel B' is at a cross point of the reference sensor 33 and a line that connects between the pixel B and the X-ray source 30. The output of the measurement sensor 31 at the pixel A is corrected by using the output of the reference sensor 33 at the pixel A'. The output of the measurement sensor 31 at the pixel B is corrected by using the output of the reference sensor 33 at the pixel B'. Then, the distribution of the detection range of the measurement sensor 31 is corrected. Specifically, a difference between the output value of the reference sensor 33 and the output value of the measurement sensor 31 is calculated in real time, an unstable component of the X-ray source is removed, and the transmission characteristics of the inspection target 32 can be measured highly accurately. The calculation unit 23 performs the calculation of the difference between the output value of the reference sensor 33 and the output value of the measurement sensor 31.

The calculation of the difference is not performed continuously at the time of measurement, but is performed in a periodical cycle. The correction is performed for a certain period of time by using the same correction value till the next calculation is performed. The X-ray control unit 26 performs the correction. The apparatus that performs the correction and the correction equation used in the correction are those of prior arts, and a description thereof will be omitted.

By using the X-ray inspection apparatus in accordance with the first preferred embodiment of the present invention, as described above:

1. The distribution change or the uniformity of the X-ray, which is irradiated radially from the X-ray source 30, can be detected. The absorbed amount of the X-ray in the inspection target 32 can be calculated in real time by calculating the difference between the measurement value of the measurement sensor 31 and the measurement value of the reference sensor 33 at each detecting element.
2. The sensitivity of the measurement can be improved.
3. The effect of temperature, humidity and change in atmospheric pressure can be excluded, and a stable result of the measurement can be expected.
4. Even if the measurement sensor 31 is in planate, the correction can be performed.

Second Preferred Embodiment

Figure 2:
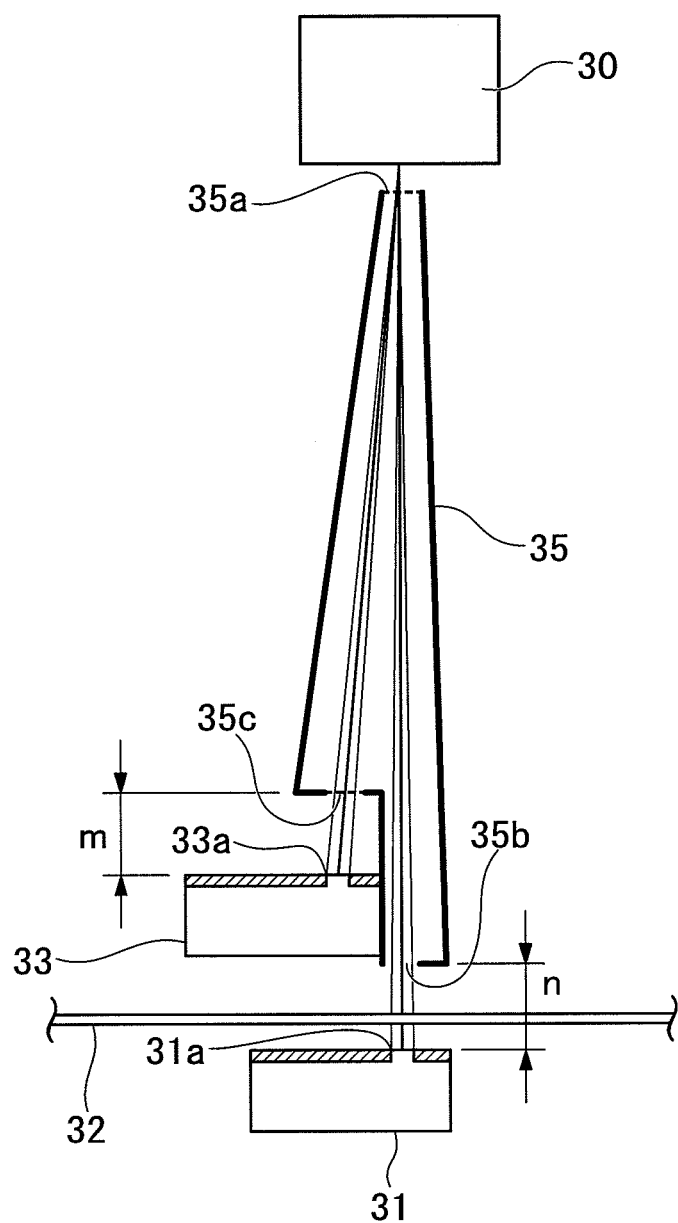
FIG. 2 is a side elevation view illustrating an X-ray inspection apparatus in accordance with a second preferred embodiment of the present invention.

A second preferred embodiment of the present invention will be described. FIG. 2 is a side elevation view illustrating the X-ray inspection apparatus in accordance with the second preferred embodiment of the present invention.

If the radiation such as the X-ray including the soft X-ray or the beta radiation is used in the inspection apparatus, then a significant amount of the radiation is absorbed by air. If the X-ray or the beta radiation is irradiated from a distance, a sufficient amount of the radiation cannot be acquired, and the measurement by the inspection apparatus is difficult. By disposing a chamber that is filled with helium (He) between the radiation source and the inspection target, the absorption of the radiation by air can be suppressed and the radiation may be irradiated from a distance.

FIG. 2 shows a construction of the X-ray inspection apparatus in accordance with the second preferred embodiment of the present invention that a helium (He) chamber 35 is added to the X-ray inspection apparatus of FIG. 1. In the second preferred embodiment of the present invention, the helium chamber 35 is disposed near the output window of the X-ray source 30. The helium chamber 35 is filled with helium. The helium chamber 35 includes an entrance window 35a from which the X-ray from the X-ray source 30 enters, an exit window 35b from which the X-ray for measurement detecting is output, and an exit window 35c from which the X-ray for reference detecting is output.

To suppress the absorption by air, the distance n between the entrance window 31a of the measurement sensor 31 and the exit window 35b of the helium chamber 35 is preferably made as small as possible. The reference sensor 33 is set so that the distance n is equal to the distance m between the entrance window 33a of the reference sensor 33 and the exit window 35c of the helium chamber 35.

By the configuration described above, the effect of the amount of the absorption by air on the measurement sensor 31 can be made equal to the effect of the amount of the absorption by air on the reference sensor 33. Therefore, the effect by temperature, humidity, atmospheric pressure and air cleanliness can be cancelled.

Third Preferred Embodiment

Figure 3:
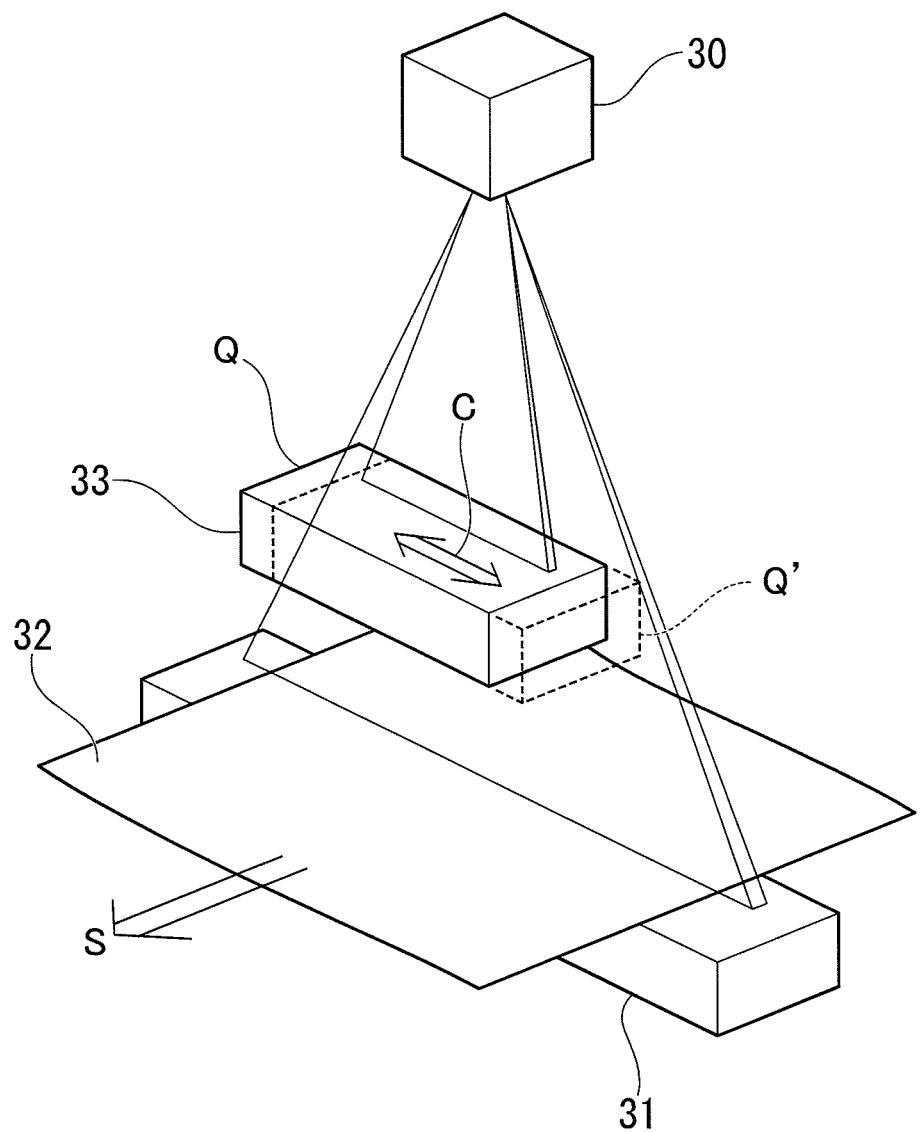
FIG. 3 is a perspective view illustrating an X-ray inspection apparatus in accordance with a third preferred embodiment of the present invention.

A third preferred embodiment of the present invention will be described. FIG. 3 is a perspective view illustrating the X-ray inspection apparatus in accordance with the third preferred embodiment of the present invention.

In the third preferred embodiment of the present invention, the reference sensor 33 moves in a direction C that is perpendicular to the direction S, which represents the direction of the movement of the inspection target 32. The reference sensor 33 is moved by using an actuator such as a cylinder and a motor, an eccentric cam and a mechanism of changing linear movement, which are not illustrated in the figure. The movement the reference sensor 33 is restricted by a linear guide, which is not illustrated in the figure, so that the height of the reference sensor 33 will not change and the reference sensor 33 will not swing. Therefore, the reference sensor 33 can move between a position Q and a position Q' of FIG. 3 precisely.

The reference sensor 33 is moved by one of an intermittent feeding and a periodic continuous reciprocating feeding. The distribution of the X-ray from the X-ray source 30 is calculated based on more than one of the measurement data at different areas of the reference sensor 33 at nearly the same time, by moving the reference sensor 33 at a comparatively fast speed, for example, by shuttling it several times a second.

The number of movement of the reference sensor 33 is counted at a plurality of measurement points that are determined based on a mechanism of the reference radiation detecting unit. The reference radiation detecting unit stops at each of the plurality of measurement points. The distribution of the X-ray from the X-ray source 30 is calculated based on more than one of the measurement data at the plurality of measurement points.

The reference sensor 33 may continuously move, the number of movement of the reference sensor 33 may be counted at different measurement points, and the distribution of the X-ray from the X-ray source 30 may be calculated based on more than one of the measurement data at the different measurement points.

More than one of the measurement data are averaged by at least one of a least squares method, an average value, moving average deviations, and combinations of more than one of the least squares method, the average value and the moving average deviations, so as to calculate a center value with a minimum of deviation. The distribution of the X-ray from the X-ray source 30 is acquired based on the temporal variation of the center value.

Each time the reference sensor 33 moves, the output data of the reference sensor 33 is stored in a storage unit. Measurement error, which results from the sensing error of the detecting elements of the reference sensor 33, is calculated based on at least more than one of the measurement data. The distribution of the X-ray from the X-ray source 30 is acquired by deducting the measurement error from the output of the reference sensor 33. If a time-series variation of the distribution of the X-ray from the X-ray source 30 is confirmed, then the output of the measurement sensor 31 is corrected based on the variation value of the distribution of the X-ray from the X-ray source 30.

Figure 4A:
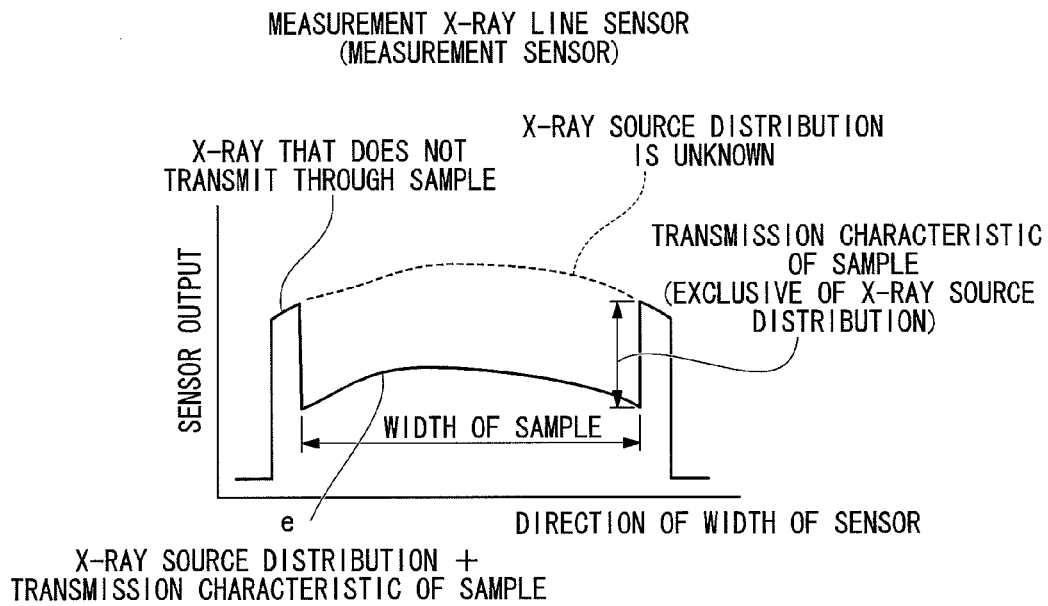
FIG. 4A is a graph illustrating a relationship between an output of a measurement X-ray line sensor and a position across-the-width of the measurement X-ray line sensor in the X-ray inspection apparatus of FIG. 3.
Figure 4B:
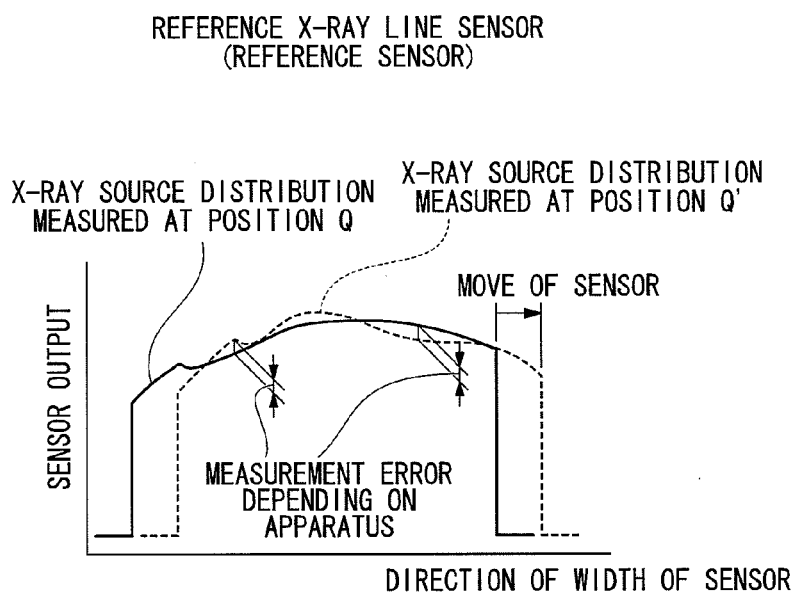
FIG. 4B is a graph illustrating a relationship between an output of a reference X-ray line sensor and a position across-the-width of the reference X-ray line sensor in the X-ray inspection apparatus of FIG. 3.

FIG. 4A is a graph illustrating a relationship between an output of the measurement sensor 31 and a position across-the-width of the measurement sensor 31 in the X-ray inspection apparatus of FIG. 3. FIG. 4B is a graph illustrating a relationship between an output of the reference sensor 33 and a position across-the-width of the reference sensor 33 in the X-ray inspection apparatus of FIG. 3.

The X-ray that is transmitted through the outside of the inspection target 32 and reaches the measuring sensor 31 is not made attenuated by the inspection target 32, and the output value of the measuring sensor 31 becomes high. The waveform of an output e of the measuring sensor 31 is low at the central part of the waveform, which corresponds to the X-ray that is transmitted through the inspection target 32, and high at both ends of the waveform, which corresponds to the X-ray that is not transmitted through the inspection target 32. The output of the measurement sensor 31 includes the effect of the distribution or the uniformity of the X-ray source 30 and the absorption characteristic or the uneven thickness of the inspection target 32. In the measurement by the measurement sensor 31, it is assumed that the distribution of the X-ray source 30, which is measured beforehand when the correction by the X-ray inspection apparatus is performed, does not change temporally.

If the intensity or the intensity distribution of the X-ray source 30 changes on the way, then the thickness of the inspection target 32 is measured incorrectly. The output change or the sensitivity variation of the X-ray source 30 or the measurement sensor 31, which is caused by a temperature or an atmospheric pressure, can be controlled by feedback, if the output change of the both ends of the measurement sensor 31, which corresponds to the X-ray that is not transmitted through the inspection target 32, is monitored. But the distribution of the X-ray source 30 can not be controlled.

Therefore, the output change of the measurement sensor 31 at both ends of the waveform is precisely measured.

The output of the reference sensor 33, which is illustrated in FIG. 4B, shows that the distribution of the X-ray is measured all over the reference sensor 33 though the individual form of the reference sensor 33 varies. If the change of the distribution is monitored, then the distribution of the X-ray source 30 can be acquired in real time.

If the change of the X-ray source 30 monitored by the reference sensor 33 is fed back to the measurement sensor 31, then the transmission characteristic of the inspection target 32, which has corrected the variation of the X-ray source, can be measured in real time. The result caused by the change of the characteristic of the reference sensor 33 may be fed back as the change of the distribution of the X-ray source 30, for the measuring sensor 31 is different from the reference sensor 33. The change of the characteristic results from the partial deterioration of the scintillator, for example.

To avoid the above phenomenon, the reference sensor 33 is moved in the direction C between the position Q and the position Q'. The direction C is perpendicular to the direction S in which the inspection target 32 is transmitted. Then, a plurality of detecting elements that are at different positions measure the intensity of the same X-ray. The difference of the intensities measured by two different detecting elements is regarded as the sensitivity error of the reference sensor 33, and can be removed from consideration.

To measure the intensity of the same X-ray by changing the position of the reference sensor 33, the reference sensor 33 is preferably moved at a comparatively fast pace. The intensity distribution that is removed of the component of the measurement error of the reference sensor 33 is acquired as the distribution of the X-ray source 30. In the above description, the reference sensor 33 measured the intensity of the X-ray at two positions, the position Q and the position Q'. The number of the positions where the reference sensor 33 measure the intensity of the X-ray is not limited to two, and may be more than two. By measuring the intensity of the X-ray at many positions, the sensitivity error of the reference sensor 33 can be removed highly accurately. The reading speed that corresponds to the exposure time of the detecting elements in the reference sensor 33 is fast enough, for example, a few thousands times per second. The intermittent feeding is not necessarily needed, and the reference sensor 33 may always move back and forth.

Fourth Preferred Embodiment

Figure 5:
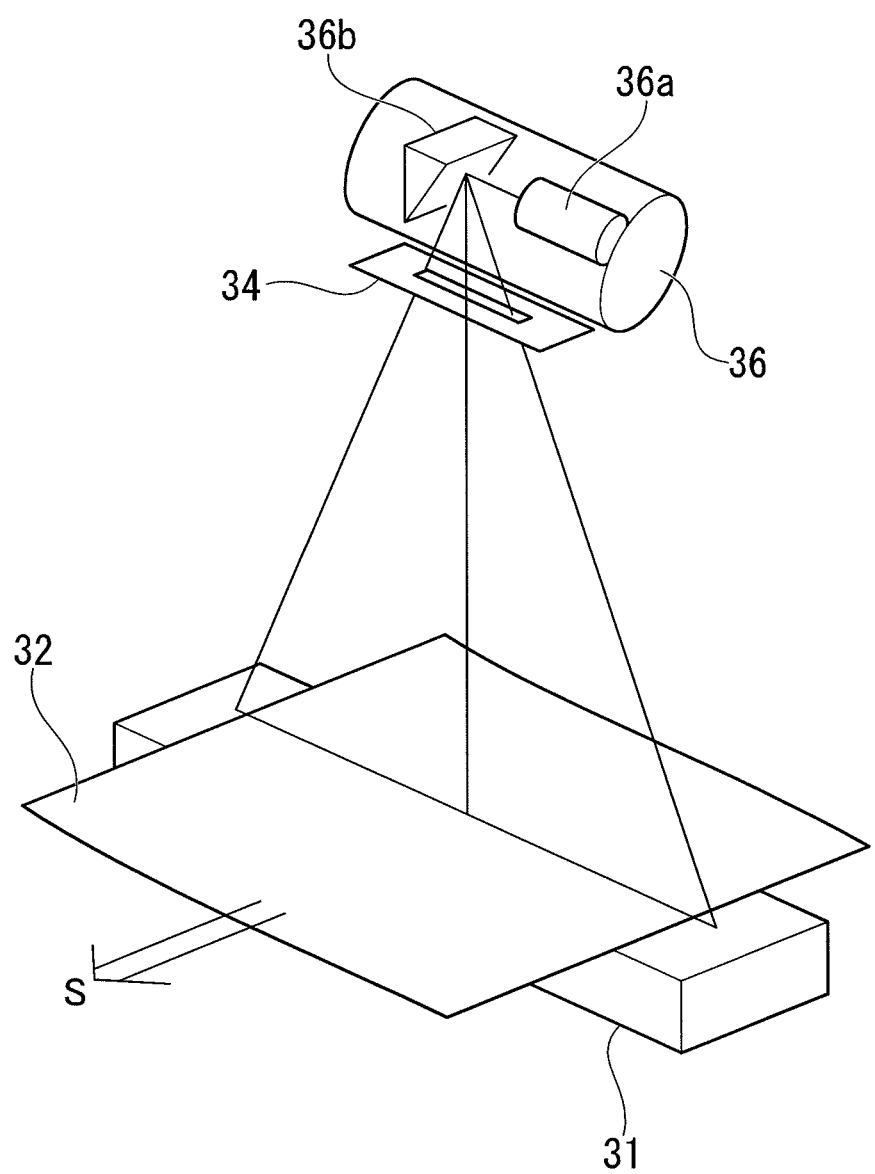
FIG. 5 is a perspective view illustrating an X-ray inspection apparatus in accordance with a fourth preferred embodiment of the present invention.
Figure 6A:
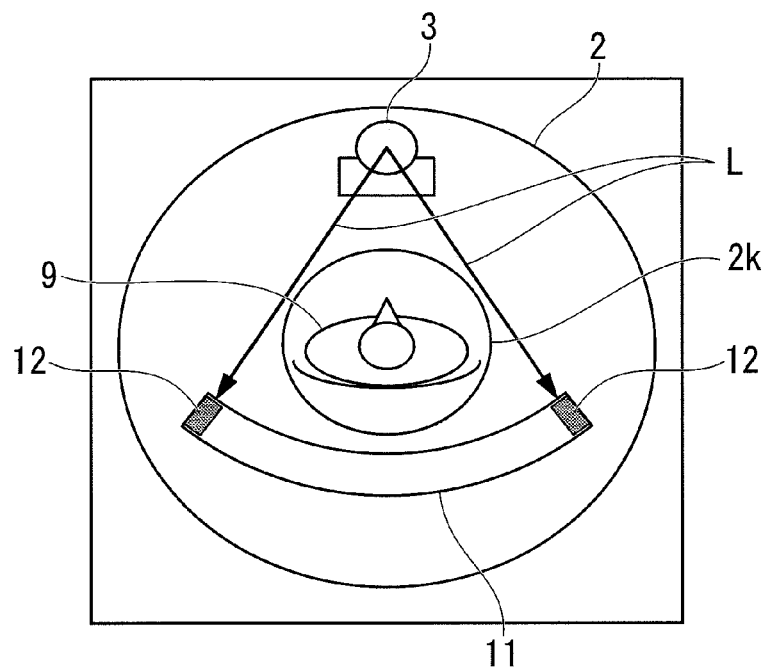
FIG. 6A is a view illustrating a configuration structure of a reference detecting element in an X-ray inspection apparatus in accordance with the related art.
Figure 6B:
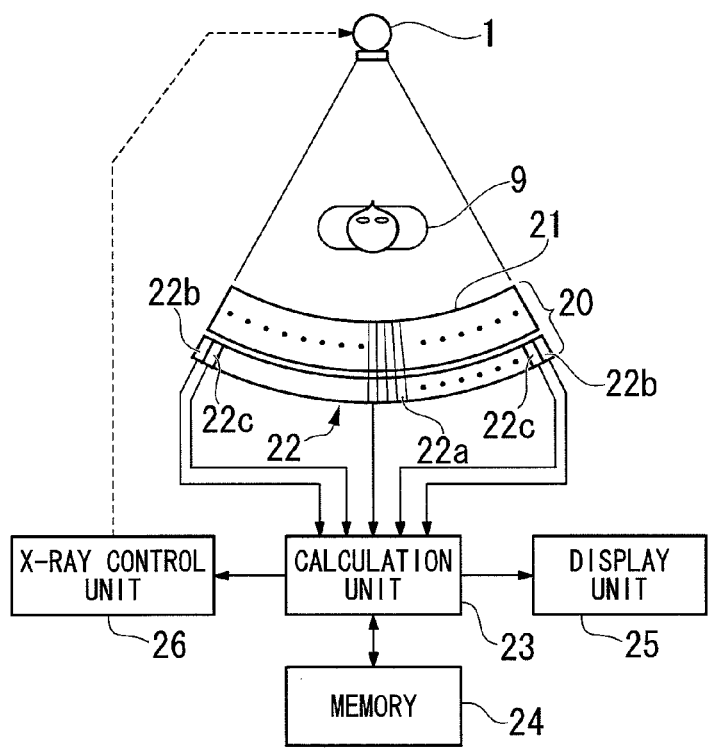
FIG. 6B is a block diagram illustrating a configuration structure of a reference detecting element in an X-ray inspection apparatus in accordance with the related art.
Figure 7:
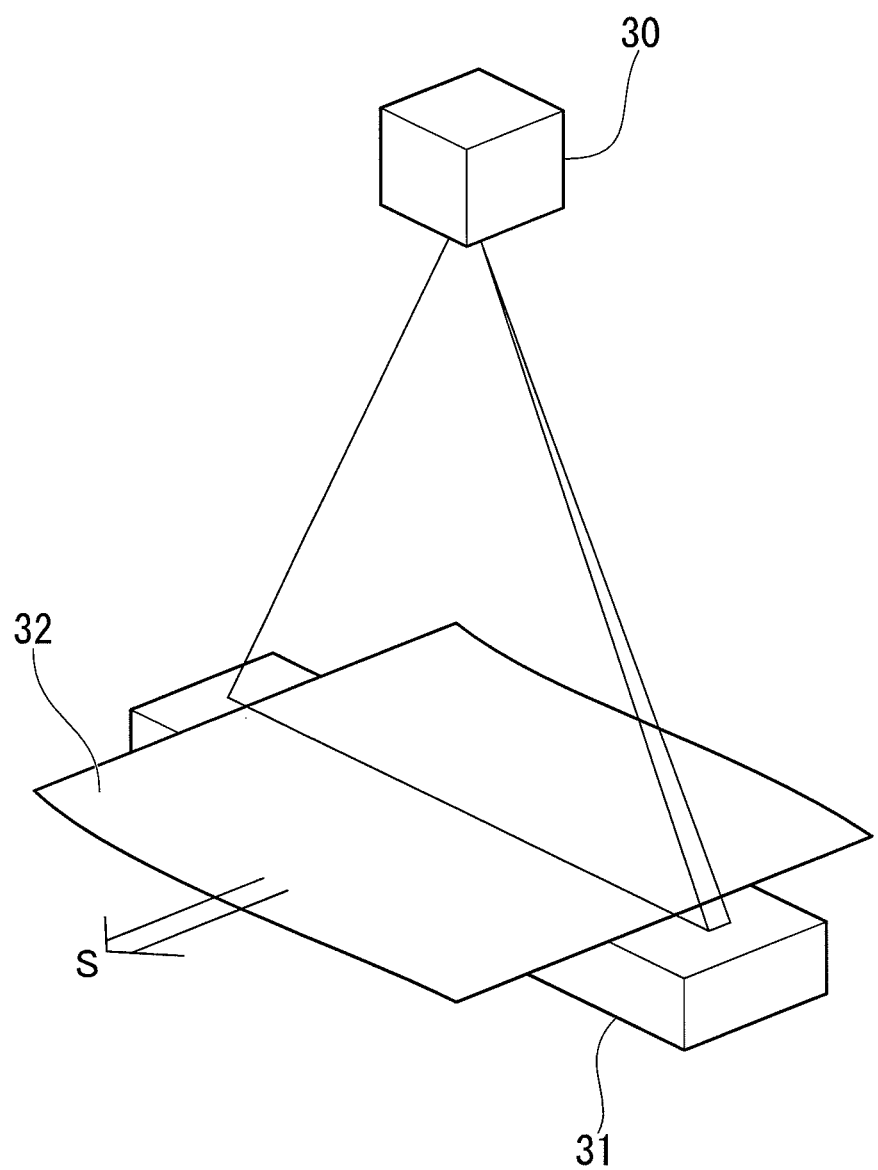
FIG. 7 is a perspective view illustrating a configuration structure of an X-ray inspection apparatus when an inspection target is sheet-shaped and is measured by an X-ray line sensor disposed in planate.

A fourth preferred embodiment of the present invention will be described. FIG. 5 is a perspective view illustrating the X-ray inspection apparatus in accordance with the fourth preferred embodiment of the present invention. In the fourth preferred embodiment, a reflection-type X-ray tube 36 is used as the X-ray source. The inspection target 32 is a sheet-shaped object. The reflection-type X-ray tube 36 includes a gun 36a that irradiates the X-ray and a target 36b that reflects the X-ray from the gun 36a. A reflection surface of the target 36b, by which the X-ray is reflected, is nearly parallel to a direction of a movement of the inspection target 32.

As used herein, the following directional terms "forward, rearward, above, downward, vertical, horizontal, below, and transverse" as well as any other similar directional terms refer to those directions of an apparatus equipped with the present invention. Accordingly, these terms, as utilized to describe the present invention should be interpreted relative to an apparatus equipped with the present invention.

The term "configured" is used to describe a component, section or part of a device includes hardware and/or software that is constructed and/or programmed to carry out the desired function.

Moreover, terms that are expressed as "means-plus function" in the claims should include any structure that can be utilized to carry out the function of that part of the present invention.

The terms of degree such as "substantially," "about," "nearly", and "approximately" as used herein mean a reasonable amount of deviation of the modified term such that the end result is not significantly changed. For example, these terms can be construed as including a deviation of at least ±5 percents of the modified term if this deviation would not negate the meaning of the word it modifies.

While preferred embodiments of the invention have been described and illustrated above, it should be understood that these are exemplary of the invention and are not to be considered as limiting. In the preferred embodiments described above, the radiation that is irradiated from the radiation source of the radiation inspection apparatus was the X-ray, but the radiation may be beta radiation or the like. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A radiation inspection apparatus that inspects an inspection target using a radiation from a radiation source comprising:
 a measurement radiation detecting unit that detects the radiation;
 a reference radiation detecting unit that detects the radiation from the radiation source, the reference radiation detecting unit being disposed between the radiation source and the inspection target;
 a calculation unit that calculates a change value of the intensity of the radiation based on an output of the reference radiation detecting unit; and
 a radiation control unit that corrects the intensity of the radiation by correcting an output of the measurement radiation detecting unit based on the change value,
 wherein the measurement radiation detecting unit being a line sensor.

2. The radiation inspection apparatus according to claim 1, further comprising:
 a radiation source unit that irradiates the radiation radially.

3. The radiation inspection apparatus according to claim 1, wherein the reference radiation detecting unit is adjacent to a path of the radiation from the radiation source to the measurement radiation detecting unit to prevent the reference radiation detecting unit from interrupting the radiation from the radiation source to the measurement radiation detecting unit.

4. The radiation inspection apparatus according to claim 1, wherein the measurement radiation detecting unit and the reference radiation detecting unit shares a same hardware component.

5. The radiation inspection apparatus according to claim 1, wherein the reference radiation detecting unit is a photosensor including a scintillator.

6. The radiation inspection apparatus according to claim 1, wherein a time-series variation of the output of the reference radiation detecting unit is calculated in real time, and the output of the measurement radiation detecting unit is corrected in real time based on a calculation result of the time-series variation of the output of the reference radiation detecting unit.

7. The radiation inspection apparatus according to claim 1, wherein if the radiation source is made of a radiation tube in reflection type that irradiates the radiation and a radiation target that reflects the radiation from the radiation tube and a sheet-shaped object is used as the inspection target, then a reflection surface of the radiation target is nearly parallel to a direction of a movement of the sheet-shaped object, the radiation being reflected by the reflection surface.

8. A radiation inspection apparatus that inspects an inspection target using a radiation from a radiation source comprising:
 a measurement radiation detecting unit that detects the radiation;
 a reference radiation detecting unit that detects the radiation from the radiation source, the reference radiation detecting unit being disposed between the radiation source and the inspection target;
 a calculation unit that calculates a change value of the intensity of the radiation based on an output of the reference radiation detecting unit; and
 a radiation control unit that corrects the intensity of the radiation by correcting an output of the measurement radiation detecting unit based on the change value,
 wherein the reference radiation detecting unit is in a rectangle shape and is different from the measurement radiation detecting unit in a size, a pitch and a length of a detecting element.

9. A radiation inspection apparatus that inspects an inspection target using a radiation from a radiation source comprising:
 a measurement radiation detecting unit that detects the radiation;
 a reference radiation detecting unit that detects the radiation from the radiation source, the reference radiation detecting unit being disposed between the radiation source and the inspection target;

a calculation unit that calculates a change value of the intensity of the radiation based on an output of the reference radiation detecting unit; and a radiation control unit that corrects the intensity of the radiation by correcting an output of the measurement radiation detecting unit based on the change value, wherein a time-series variation of the output of the reference radiation detecting unit is calculated at a constant period, and the output of the measurement radiation detecting unit is corrected based on a same correction value of a calculation result of the time-series variation of the output of the reference radiation detecting unit till a next calculation of the time-series variation of the output of the reference radiation detecting unit is performed.

10. A radiation inspection apparatus that inspects an inspection target using a radiation from a radiation source comprising:

a measurement radiation detecting unit that detects the radiation;

a reference radiation detecting unit that detects the radiation from the radiation source, the reference radiation detecting unit being disposed between the radiation source and the inspection target;

a calculation unit that calculates a change value of the intensity of the radiation based on an output of the reference radiation detecting unit; and a radiation control unit that corrects the intensity of the radiation by correcting an output of the measurement radiation detecting unit based on the change value, wherein a sealed structure is disposed between the radiation source and the inspection target, the sealed structure is filled with a gas, the sealed structure includes an entrance window of the radiation from the radiation source, a first exit window that outputs the radiation for measurement detecting to the measurement radiation detecting unit, and a second exit window that outputs the radiation for reference detecting to the reference radiation detecting unit.

11. The radiation inspection apparatus according to claim 10, wherein a first distance between the first exit window and the measurement radiation detecting unit is equal to a second distance between the second exit window and the reference radiation detecting unit.

12. A radiation inspection apparatus that inspects an inspection target using a radiation from a radiation source comprising:

a measurement radiation detecting unit that detects the radiation;

a reference radiation detecting unit that detects the radiation from the radiation source, the reference radiation detecting unit being disposed between the radiation source and the inspection target;

a calculation unit that calculates a change value of the intensity of the radiation based on an output of the reference radiation detecting unit; and a radiation control unit that corrects the intensity of the radiation by correcting an output of the measurement radiation detecting unit based on the change value, wherein a collimator is disposed adjacent to the radiation source, and the collimator includes a first irradiating window that outputs the radiation for measurement detecting and a second irradiating window that outputs the radiation for reference detecting.

13. A radiation inspection apparatus that inspects an inspection target using a radiation from a radiation source comprising:

a measurement radiation detecting unit that detects the radiation;

a reference radiation detecting unit that detects the radiation from the radiation source, the reference radiation detecting unit being disposed between the radiation source and the inspection target;

a calculation unit that calculates a change value of the intensity of the radiation based on an output of the reference radiation detecting unit; and a radiation control unit that corrects the intensity of the radiation by correcting an output of the measurement radiation detecting unit based on the change value, wherein the reference radiation detecting unit is moved in one of a direction that is parallel to at least one of a long side of the measurement radiation detecting unit and a row of a plurality of photodiodes and a direction that is nearly perpendicular to a movement of the inspection target, the output of the reference radiation detecting unit is stored in a storage unit as measurement data every time the reference radiation detecting unit is moved, a measurement error of the reference radiation detecting unit is calculated based on more than one of the measurement data of the reference radiation detecting unit, and if time-series variation of the intensity distribution of the radiation source is confirmed, then the output of the measurement radiation detecting unit is corrected based on the time-series variation, the intensity distribution being acquired by deducting the measurement error from the measurement data of the reference radiation detecting unit.

14. The radiation inspection apparatus according to claim 13, wherein the reference radiation detecting unit is moved by one of an intermittent feeding and a periodic continuous reciprocating feeding, and the intensity distribution of the radiation source is calculated based on more than one of the measurement data at different areas of the reference radiation detecting unit at nearly a same time.

15. The radiation inspection apparatus according to claim 13, wherein the number of movement of the reference radiation detecting unit is measured at a plurality of measurement points, the plurality of measurement points are determined based on a mechanism of the reference radiation detecting unit, the reference radiation detecting unit stops at each of the plurality of measurement points, the intensity distribution of the radiation source is calculated based on more than one of the measurement data at the plurality of measurement points.

16. The radiation inspection apparatus according to claim 13, wherein the reference radiation detecting unit continuously moves, the number of movement of the reference radiation detecting unit is measured at different measurement points, the intensity distribution of the radiation source is calculated based on more than one of the measurement data at the different measurement points.

17. The radiation inspection apparatus according to claim 13, wherein more than one of the measurement data are averaged by at least one of a least squares method, an average value, moving average deviations, and combinations of more than one of the least squares method, the average value and the moving average deviations, so as to calculate a center value with a minimum of deviation, and the intensity distribution of the radiation source is acquired based on a temporal variation of the center value.

* * * * *